US008557077B2

(12) United States Patent
Coose et al.

(10) Patent No.: US 8,557,077 B2
(45) Date of Patent: Oct. 15, 2013

(54) METHOD OF PRODUCING A PANTS-TYPE DIAPER

(75) Inventors: Thomas R. Coose, Plymouth, WI (US); John A. McCabe, Sheboygan Falls, WI (US); Peter J. Jenquin, Plymouth, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 0 days.

(21) Appl. No.: 13/052,740

(22) Filed: Mar. 21, 2011

(65) Prior Publication Data

US 2011/0168326 A1    Jul. 14, 2011

Related U.S. Application Data

(63) Continuation of application No. 12/583,042, filed on Aug. 13, 2009, now Pat. No. 7,909,956, which is a continuation-in-part of application No. 11/083,765, filed on Mar. 18, 2005, now Pat. No. 7,638,014.

(60) Provisional application No. 60/573,648, filed on May 21, 2004.

(51) Int. Cl.
 *B32B 38/04* (2006.01)
(52) U.S. Cl.
 USPC .................. 156/250; 156/265; 156/270
(58) Field of Classification Search
 USPC ......... 156/161, 179, 229, 250, 257, 260, 265, 156/270, 436
 See application file for complete search history.

(56) References Cited

U.S. PATENT DOCUMENTS

| 135,145 A | 1/1873 | Murphy |
| 293,353 A | 2/1884 | Purvis |
| 312,257 A | 2/1885 | Cotton et al. |
| 410,123 A | 8/1889 | Stilwell |
| 432,742 A | 7/1890 | Stanley |
| 643,821 A | 2/1900 | Howlett |
| 1,393,524 A | 10/1921 | Grupe |
| 1,431,315 A | 10/1922 | Le Moine |
| 1,605,842 A | 2/1926 | Jones |
| 1,686,595 A | 10/1928 | Belluche |
| 1,957,651 A | 5/1934 | Joa |
| 2,009,857 A | 7/1935 | Potdevin |
| 2,054,832 A | 9/1936 | Potdevin |
| 2,117,432 A | 5/1938 | Linscott |
| 2,128,746 A | 8/1938 | Joa |
| 2,131,808 A | 10/1938 | Joa |

(Continued)

FOREIGN PATENT DOCUMENTS

| BE | 1007854 | 11/1995 |
| CA | 1146129 | 5/1983 |

(Continued)

OTHER PUBLICATIONS

Reciprocating Mechanisms, Ingenious Mechanisms for Designers and Inventors, Franklin Jones vol. 1.

(Continued)

*Primary Examiner* — Sing P Chan
(74) *Attorney, Agent, or Firm* — Ryan Kromholz & Manion, S.C.

(57) ABSTRACT

A method for producing disposable undergarments is disclosed. The method generally comprises combining a first layer, comprising an elastic material sandwiched between layers of nonwoven material, and a second layer, comprising a backing material and a graphically printed applied patch of material layer.

6 Claims, 5 Drawing Sheets

(56) References Cited

U.S. PATENT DOCUMENTS

| | | |
|---|---|---|
| 2,171,741 A | 5/1939 | Cohn et al. |
| 2,164,408 A | 7/1939 | Joa |
| 2,167,179 A | 7/1939 | Joa |
| 2,213,431 A | 9/1940 | Joa |
| 2,254,290 A | 9/1941 | Joa |
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,627,859 A | 2/1953 | Hargrave |
| 2,695,025 A | 11/1954 | Andrews |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,788,786 A | 4/1957 | Dexter |
| 2,811,905 A | 11/1957 | Kennedy, Jr. |
| 2,828,745 A | 4/1958 | Deutz |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,890,700 A | 6/1959 | Lonberg-Holm |
| 2,913,862 A | 11/1959 | Sabee |
| 2,939,461 A | 6/1960 | Joa |
| 2,939,646 A | 6/1960 | Stone |
| 2,960,143 A | 11/1960 | Joa |
| 2,990,081 A | 6/1961 | Neui et al. |
| 2,991,739 A | 7/1961 | Joa |
| 3,016,207 A | 1/1962 | Comstock |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,089,494 A | 5/1963 | Schwartz |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa et al. |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,318,608 A | 5/1967 | Smrekar |
| 3,322,589 A | 5/1967 | Joa |
| 3,342,184 A | 9/1967 | Joa |
| 3,356,092 A | 12/1967 | Joa |
| 3,360,103 A | 12/1967 | Johnson |
| 3,363,847 A | 1/1968 | Joa |
| 3,391,777 A | 7/1968 | Joa |
| 3,454,442 A | 7/1969 | Heller, Jr. |
| 3,463,413 A | 8/1969 | Smith |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo et al. |
| 3,575,170 A | 4/1971 | Clark |
| 3,607,578 A | 9/1971 | Berg et al. |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger |
| 3,728,191 A | 4/1973 | Wierzba et al. |
| 3,751,224 A | 8/1973 | Wackerle |
| 3,758,102 A | 9/1973 | Munn et al. |
| 3,772,120 A | 11/1973 | Radzins |
| 3,776,798 A | 12/1973 | Milano |
| 3,796,360 A | 3/1974 | Alexeff |
| 3,811,987 A | 5/1974 | Wilkinson et al. |
| 3,816,210 A | 6/1974 | Aoko et al. |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,901,238 A | 8/1975 | Gellert et al. |
| 3,903,768 A | 9/1975 | Amberg |
| 3,904,147 A | 9/1975 | Taitel et al. |
| 3,918,698 A | 11/1975 | Coast |
| 3,960,646 A | 6/1976 | Wiedamann |
| 3,988,194 A | 10/1976 | Babcock et al. |
| 3,991,994 A | 11/1976 | Farish |
| 4,002,005 A | 1/1977 | Mueller et al. |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,222,533 A | 9/1980 | Pongracz |
| 4,223,822 A | 9/1980 | Clitheroe |
| 4,231,129 A | 11/1980 | Winch |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A | 2/1982 | Wilson |
| 4,325,519 A | 4/1982 | McLean |
| 4,342,206 A | 8/1982 | Rommel |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,452,597 A | 6/1984 | Achelpohl |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,543,152 A | 9/1985 | Nozaka |
| 4,551,191 A | 11/1985 | Kock et al. |
| 4,586,199 A | 5/1986 | Birring |
| 4,589,945 A | 5/1986 | Polit |

(56) References Cited

U.S. PATENT DOCUMENTS

| | | |
|---|---|---|
| 4,603,800 A | 8/1986 | Focke et al. |
| 4,608,115 A | 8/1986 | Schroth et al. |
| 4,610,681 A | 9/1986 | Strohbeen et al. |
| 4,610,682 A | 9/1986 | Kopp |
| 4,614,076 A | 9/1986 | Rathmacher |
| 4,619,357 A | 10/1986 | Radzins et al. |
| 4,634,482 A | 1/1987 | Lammers |
| 4,641,381 A | 2/1987 | Heran et al. |
| 4,642,150 A | 2/1987 | Stemmler |
| 4,642,839 A | 2/1987 | Urban |
| 4,650,530 A | 3/1987 | Mahoney et al. |
| 4,663,220 A | 5/1987 | Wisnecki et al. |
| 4,672,705 A | 6/1987 | Bors et al. |
| 4,675,016 A | 6/1987 | Meuli et al. |
| 4,675,062 A | 6/1987 | Instance |
| 4,675,068 A | 6/1987 | Lundmark |
| 4,686,136 A | 8/1987 | Homonoff et al. |
| 4,693,056 A | 9/1987 | Raszewski |
| 4,701,239 A | 10/1987 | Craig |
| 4,720,415 A | 1/1988 | Vander Wielen et al. |
| 4,723,698 A | 2/1988 | Schoonderbeek |
| 4,726,874 A | 2/1988 | VanVliet |
| 4,726,876 A | 2/1988 | Tomosovic et al. |
| 4,743,241 A | 5/1988 | Igaue et al. |
| 4,751,997 A | 6/1988 | Hirsch |
| 4,753,429 A | 6/1988 | Irvine et al. |
| 4,756,141 A | 7/1988 | Hirsch et al. |
| 4,764,325 A | 8/1988 | Angstadt |
| 4,765,780 A | 8/1988 | Angstadt |
| 4,776,920 A | 10/1988 | Ryan |
| 4,777,513 A | 10/1988 | Nelson |
| 4,782,647 A | 11/1988 | Williams et al. |
| 4,785,986 A | 11/1988 | Daane et al. |
| 4,795,451 A | 1/1989 | Buckley |
| 4,795,510 A | 1/1989 | Wittrock et al. |
| 4,798,353 A | 1/1989 | Peugh |
| 4,801,345 A | 1/1989 | Dussaud et al. |
| 4,802,570 A | 2/1989 | Hirsch et al. |
| 4,840,609 A | 6/1989 | Jones et al. |
| 4,845,964 A | 7/1989 | Bors et al. |
| 4,864,802 A | 9/1989 | D'Angelo |
| 4,880,102 A | 11/1989 | Indrebo |
| 4,888,231 A | 12/1989 | Angstadt |
| 4,892,536 A | 1/1990 | Des Marais et al. |
| 4,904,440 A | 2/1990 | Angstadt |
| 4,908,175 A | 3/1990 | Angstadt |
| 4,909,019 A | 3/1990 | Delacretaz et al. |
| 4,915,767 A | 4/1990 | Rajala et al. |
| 4,917,746 A | 4/1990 | Kons |
| 4,925,520 A | 5/1990 | Beaudoin et al. |
| 4,927,322 A | 5/1990 | Schweizer et al. |
| 4,927,486 A | 5/1990 | Fattal et al. |
| 4,927,582 A | 5/1990 | Bryson |
| 4,937,887 A | 7/1990 | Schreiner |
| 4,963,072 A | 10/1990 | Miley et al. |
| 4,987,940 A | 1/1991 | Straub et al. |
| 4,994,010 A | 2/1991 | Doderer-Winkler |
| 5,000,806 A | 3/1991 | Merkatoris et al. |
| 5,021,111 A | 6/1991 | Swenson |
| 5,025,910 A | 6/1991 | Lasure et al. |
| 5,045,039 A | 9/1991 | Bay |
| 5,062,597 A | 11/1991 | Martin et al. |
| 5,064,179 A | 11/1991 | Martin |
| 5,064,492 A | 11/1991 | Friesch |
| 5,080,741 A | 1/1992 | Nomura et al. |
| 5,094,658 A | 3/1992 | Smithe et al. |
| 5,096,532 A | 3/1992 | Neuwirth et al. |
| 5,108,017 A | 4/1992 | Adamski et al. |
| 5,109,767 A | 5/1992 | Nyfeler et al. |
| 5,110,403 A | 5/1992 | Ehlert |
| 5,127,981 A | 7/1992 | Straub et al. |
| 5,131,525 A | 7/1992 | Musschoot |
| 5,131,901 A | 7/1992 | Moll |
| 5,133,511 A | 7/1992 | Mack et al. |
| 5,139,713 A | 8/1992 | Voshimura et al. |
| 5,147,487 A | 9/1992 | Nomura et al. |
| 5,163,594 A | 11/1992 | Meyer |
| 5,171,239 A | 12/1992 | Igaue et al. |
| 5,176,244 A | 1/1993 | Radzins et al. |
| 5,183,252 A | 2/1993 | Wolber et al. |
| 5,188,627 A | 2/1993 | Igaue et al. |
| 5,190,234 A | 3/1993 | Ezekiel |
| 5,195,684 A | 3/1993 | Radzins |
| 5,203,043 A | 4/1993 | Riedel |
| 5,213,645 A | 5/1993 | Nomura et al. |
| 5,222,422 A | 6/1993 | Benner, Jr. et al. |
| 5,223,069 A | 6/1993 | Tokuno et al. |
| 5,226,992 A | 7/1993 | Morman |
| 5,246,433 A | 9/1993 | Hasse et al. |
| 5,252,170 A | 10/1993 | Schaupp |
| 5,267,933 A | 12/1993 | Precoma |
| 5,273,228 A | 12/1993 | Yoshida et al. |
| 5,275,676 A | 1/1994 | Rooyakkers et al. |
| 5,308,345 A | 5/1994 | Herrin |
| 5,328,438 A | 7/1994 | Crowley |
| 5,340,424 A | 8/1994 | Matsushita |
| 5,368,893 A | 11/1994 | Sommer et al. |
| 5,389,173 A | 2/1995 | Merkatoris et al. |
| 5,393,360 A | 2/1995 | Bridges et al. |
| 5,407,507 A | 4/1995 | Ball |
| 5,407,513 A | 4/1995 | Hayden et al. |
| 5,415,649 A | 5/1995 | Watanabe et al. |
| 5,421,924 A | 6/1995 | Ziegelhoffer et al. |
| 5,429,576 A | 7/1995 | Doderer-Winkler |
| 5,435,802 A | 7/1995 | Kober |
| 5,449,353 A | 9/1995 | Watanabe et al. |
| 5,464,401 A | 11/1995 | Hasse et al. |
| 5,486,253 A | 1/1996 | Otruba |
| 5,494,622 A | 2/1996 | Heath et al. |
| 5,500,075 A | 3/1996 | Herrmann |
| 5,516,392 A | 5/1996 | Bridges et al. |
| 5,518,566 A | 5/1996 | Bridges et al. |
| 5,525,175 A | 6/1996 | Blenke et al. |
| 5,527,205 A | 6/1996 | Heath et al. |
| 5,531,850 A | 7/1996 | Hermann |
| 5,540,647 A | 7/1996 | Weiermann et al. |
| 5,545,275 A | 8/1996 | Herrin et al. |
| 5,545,285 A | 8/1996 | Johnson |
| 5,552,013 A | 9/1996 | Ehlert et al. |
| 5,556,360 A | 9/1996 | Kober et al. |
| 5,556,504 A | 9/1996 | Rajala et al. |
| 5,560,793 A | 10/1996 | Ruscher et al. |
| 5,575,187 A | 11/1996 | Dieterlen |
| 5,586,964 A | 12/1996 | Chase |
| 5,602,747 A | 2/1997 | Rajala |
| 5,603,794 A | 2/1997 | Thomas |
| 5,624,420 A | 4/1997 | Bridges et al. |
| 5,624,428 A | 4/1997 | Sauer |
| 5,628,738 A | 5/1997 | Suekane |
| 5,634,917 A | 6/1997 | Fujioka et al. |
| 5,643,165 A | 7/1997 | Klekamp |
| 5,643,396 A | 7/1997 | Rajala et al. |
| 5,645,543 A | 7/1997 | Nomura et al. |
| 5,659,229 A | 8/1997 | Rajala |
| 5,660,657 A | 8/1997 | Rajala et al. |
| 5,660,665 A | 8/1997 | Jalonen |
| 5,683,376 A | 11/1997 | Kato et al. |
| 5,683,531 A | 11/1997 | Roessler et al. |
| RE35,687 E | 12/1997 | Igaue et al. |
| 5,693,165 A | 12/1997 | Schmitz |
| 5,699,653 A | 12/1997 | Hartman et al. |
| 5,705,013 A | 1/1998 | Nease |
| 5,707,470 A | 1/1998 | Rajala et al. |
| 5,711,832 A | 1/1998 | Glaug et al. |
| 5,725,518 A | 3/1998 | Coates |
| 5,725,714 A | 3/1998 | Fujioka |
| 5,743,994 A | 4/1998 | Roessler et al. |
| 5,745,922 A | 5/1998 | Rajala et al. |
| 5,746,869 A | 5/1998 | Hayden et al. |
| 5,749,989 A | 5/1998 | Linman et al. |
| 5,766,389 A | 6/1998 | Brandon et al. |
| 5,788,797 A | 8/1998 | Herrin et al. |
| 5,817,199 A | 10/1998 | Brennecke et al. |
| 5,829,164 A | 11/1998 | Kotitschke |

(56) References Cited

U.S. PATENT DOCUMENTS

| | | |
|---|---|---|
| 5,836,931 A | 11/1998 | Toyoda et al. |
| 5,858,012 A | 1/1999 | Yamaki et al. |
| 5,865,393 A | 2/1999 | Kreft et al. |
| 5,868,727 A | 2/1999 | Barr et al. |
| 5,876,027 A | 3/1999 | Fukui et al. |
| 5,876,792 A | 3/1999 | Caldwell |
| 5,879,500 A | 3/1999 | Herrin et al. |
| 5,902,431 A | 5/1999 | Wilkinson et al. |
| 5,932,039 A | 8/1999 | Popp et al. |
| 5,938,193 A | 8/1999 | Bluemle et al. |
| 5,964,390 A | 10/1999 | Borresen et al. |
| 5,964,970 A | 10/1999 | Woolwine et al. |
| 6,022,443 A | 2/2000 | Rajala et al. |
| 6,036,805 A | 3/2000 | McNichols |
| 6,043,836 A | 3/2000 | Kern et al. |
| 6,050,517 A | 4/2000 | Dobrescu et al. |
| 6,074,110 A | 6/2000 | Verlinden et al. |
| 6,076,442 A | 6/2000 | Arterburn et al. |
| 6,098,249 A | 8/2000 | Toney et al. |
| 6,123,792 A | 9/2000 | Samida et al. |
| 6,171,432 B1 | 1/2001 | Brisebois et al. |
| 6,183,576 B1 | 2/2001 | Couillard et al. |
| 6,195,850 B1 | 3/2001 | Melbye |
| 6,210,386 B1 | 4/2001 | Inoue |
| 6,212,859 B1 | 4/2001 | Bielik, Jr. et al. |
| 6,214,147 B1 | 4/2001 | Mortellite et al. |
| 6,250,048 B1 | 6/2001 | Linkiewicz |
| 6,264,784 B1 | 7/2001 | Menard et al. |
| 6,276,421 B1 | 8/2001 | Valenti et al. |
| 6,276,587 B1 | 8/2001 | Borresen et al. |
| 6,284,081 B1 | 9/2001 | Vogt et al. |
| 6,287,409 B1 | 9/2001 | Stephany |
| 6,306,122 B1 | 10/2001 | Narawa et al. |
| 6,309,336 B1 | 10/2001 | Muessig et al. |
| 6,312,420 B1 | 11/2001 | Sasaki et al. |
| 6,314,333 B1 | 11/2001 | Rajala et al. |
| 6,315,022 B1 | 11/2001 | Herrin et al. |
| 6,319,347 B1 | 11/2001 | Rajala |
| 6,336,921 B1 | 1/2002 | Kato et al. |
| 6,358,350 B1 | 3/2002 | Glaug et al. |
| 6,369,291 B1 | 4/2002 | Uchimoto et al. |
| 6,375,769 B1 | 4/2002 | Quereshi et al. |
| 6,391,013 B1 | 5/2002 | Suzuki et al. |
| 6,416,697 B1 | 7/2002 | Venturino et al. |
| 6,431,038 B2 | 8/2002 | Couturier |
| 6,440,246 B1 | 8/2002 | Vogt et al. |
| 6,443,389 B1 | 9/2002 | Palone |
| 6,446,795 B1 | 9/2002 | Allen et al. |
| 6,473,669 B2 | 10/2002 | Rajala et al. |
| 6,475,325 B1 | 11/2002 | Parrish et al. |
| 6,478,786 B1 | 11/2002 | Gloug et al. |
| 6,482,278 B1 | 11/2002 | McCabe et al. |
| 6,494,244 B2 | 12/2002 | Parrish et al. |
| 6,514,233 B1 | 2/2003 | Glaug |
| 6,521,320 B2 | 2/2003 | McCabe et al. |
| 6,523,595 B1 | 2/2003 | Milner et al. |
| 6,524,423 B1 | 2/2003 | Hilt et al. |
| 6,533,879 B2 | 3/2003 | Quereshi et al. |
| 6,540,857 B1 | 4/2003 | Coenen et al. |
| 6,547,909 B1 | 4/2003 | Butterworth |
| 6,551,228 B1 | 4/2003 | Richards |
| 6,551,430 B1 | 4/2003 | Glaug et al. |
| 6,554,815 B1 | 4/2003 | Umebayashi |
| 6,569,275 B1 | 5/2003 | Popp et al. |
| 6,572,520 B2 | 6/2003 | Blumle |
| 6,581,517 B1 | 6/2003 | Recker et al. |
| 6,585,841 B1 | 7/2003 | Popp et al. |
| 6,589,149 B1 | 7/2003 | VanEperen et al. |
| 6,596,107 B2 | 7/2003 | Stopher |
| 6,596,108 B2 | 7/2003 | McCabe |
| 6,605,172 B1 | 8/2003 | Anderson et al. |
| 6,605,173 B2 | 8/2003 | Glaug et al. |
| 6,637,583 B1 | 10/2003 | Andersson |
| 6,648,122 B1 | 11/2003 | Hirsch et al. |
| 6,649,010 B2 | 11/2003 | Parrish et al. |
| 6,656,309 B1 | 12/2003 | Parker et al. |
| 6,659,150 B1 | 12/2003 | Perkins et al. |
| 6,659,991 B2 | 12/2003 | Suckane |
| 6,675,552 B2 | 1/2004 | Kunz et al. |
| 6,684,925 B2 | 2/2004 | Nagate et al. |
| 6,722,494 B2 | 4/2004 | Nakakado |
| 6,730,189 B1 | 5/2004 | Franzmann |
| 6,743,324 B2 | 6/2004 | Hargett et al. |
| 6,750,466 B2 | 6/2004 | Guha et al. |
| 6,758,109 B2 | 7/2004 | Nakakado |
| 6,766,817 B2 | 7/2004 | Dias da Silva |
| 6,808,582 B2 | 10/2004 | Popp et al. |
| D497,991 S | 11/2004 | Otsubo et al. |
| 6,814,217 B2 | 11/2004 | Blumenthal et al. |
| 6,820,671 B2 | 11/2004 | Calvert |
| 6,837,840 B2 | 1/2005 | Yonekawa et al. |
| 6,840,616 B2 | 1/2005 | Summers |
| 6,852,186 B1 | 2/2005 | Matsuda et al. |
| 6,875,202 B2 | 4/2005 | Kumasaka et al. |
| 6,893,528 B2 | 5/2005 | Middelstadt et al. |
| 6,913,718 B2 | 7/2005 | Ducker |
| 6,918,404 B2 | 7/2005 | Dias da Silva |
| 6,976,521 B2 | 12/2005 | Mlinar |
| 6,978,486 B2 | 12/2005 | Zhou et al. |
| 7,017,820 B1 | 3/2006 | Brunner |
| 7,045,031 B2 | 5/2006 | Popp et al. |
| 7,066,586 B2 | 6/2006 | Dias da Silva |
| 7,077,393 B2 | 7/2006 | Ishida |
| 7,130,710 B2 | 10/2006 | Popp et al. |
| 7,172,666 B2 | 2/2007 | Groves et al. |
| 7,195,684 B2 | 3/2007 | Satoh |
| 7,201,345 B2 | 4/2007 | Werner et al. |
| 7,214,174 B2 | 5/2007 | Allen et al. |
| 7,214,287 B2 | 5/2007 | Shiomi et al. |
| 7,247,219 B2 | 7/2007 | O'Dowd |
| 7,303,708 B2 | 12/2007 | Andrews et al. |
| 7,380,213 B2 | 5/2008 | Pokorny et al. |
| 7,398,870 B2 | 7/2008 | McCabe |
| 7,449,084 B2 | 11/2008 | Nakakado |
| 7,452,436 B2 | 11/2008 | Andrews |
| 7,533,709 B2 | 5/2009 | Meyer |
| 7,537,215 B2 | 5/2009 | Beaudoin et al. |
| 7,587,966 B2 | 9/2009 | Nakakado et al. |
| 7,618,513 B2 | 11/2009 | Meyer |
| 7,638,014 B2 | 12/2009 | Coose et al. |
| 7,640,962 B2 | 1/2010 | Meyer et al. |
| 7,703,599 B2 | 4/2010 | Meyer |
| 7,708,849 B2 | 5/2010 | McCabe |
| 7,770,712 B2 | 8/2010 | McCabe |
| 7,771,407 B2 | 8/2010 | Umebayashi |
| 7,780,052 B2 | 8/2010 | McCabe |
| 7,811,403 B2 | 10/2010 | Andrews |
| 7,861,756 B2 | 1/2011 | Jenquin et al. |
| 7,871,400 B2 | 1/2011 | Sablone et al. |
| 7,909,956 B2 | 3/2011 | Coose et al. |
| 7,975,584 B2 | 7/2011 | McCabe |
| 7,987,964 B2 | 8/2011 | McCabe |
| 8,007,484 B2 | 8/2011 | McCabe et al. |
| 8,007,623 B2 | 8/2011 | Andrews |
| 8,011,493 B2 | 9/2011 | Giuliani et al. |
| 8,016,972 B2 | 9/2011 | Andrews et al. |
| 2001/0012813 A1 | 8/2001 | Bluemle |
| 2001/0017181 A1 | 8/2001 | Otruba et al. |
| 2002/0046802 A1 | 4/2002 | Tachibana et al. |
| 2002/0059013 A1 | 5/2002 | Rajala et al. |
| 2002/0096241 A1 | 7/2002 | Instance |
| 2002/0125105 A1 | 9/2002 | Nakakado |
| 2002/0162776 A1 | 11/2002 | Hergeth |
| 2003/0000620 A1 | 1/2003 | Herrin et al. |
| 2003/0015209 A1 | 1/2003 | Gingrass et al. |
| 2003/0051802 A1 | 3/2003 | Hargett |
| 2003/0052148 A1 | 3/2003 | Rajala et al. |
| 2003/0066585 A1 | 4/2003 | McCabe |
| 2003/0083638 A1 | 5/2003 | Malee |
| 2003/0084984 A1 | 5/2003 | Glaug |
| 2003/0089447 A1 | 5/2003 | Molee et al. |
| 2003/0121614 A1 | 7/2003 | Tabor |
| 2003/0135189 A1 | 7/2003 | Umebayashi |
| 2004/0007328 A1 | 1/2004 | Popp et al. |

(56) References Cited

U.S. PATENT DOCUMENTS

| | | |
|---|---|---|
| 2004/0016500 A1 | 1/2004 | Tachibana et al. |
| 2004/0044325 A1 | 3/2004 | Corneliusson |
| 2004/0087425 A1 | 5/2004 | Ng et al. |
| 2004/0112517 A1 | 6/2004 | Groves et al. |
| 2004/0164482 A1 | 8/2004 | Edinger |
| 2004/0182497 A1 | 9/2004 | Lowrey |
| 2005/0000628 A1 | 1/2005 | Norrby |
| 2005/0022476 A1 | 2/2005 | Hamer et al. |
| 2005/0077418 A1 | 4/2005 | Werner et al. |
| 2005/0196538 A1 | 9/2005 | Sommer et al. |
| 2005/0230056 A1 | 10/2005 | Meyer et al. |
| 2005/0230449 A1 | 10/2005 | Meyer et al. |
| 2005/0234412 A1 | 10/2005 | Andrews et al. |
| 2005/0245881 A1 | 11/2005 | Meyer |
| 2005/0257881 A1 | 11/2005 | Coose et al. |
| 2005/0275148 A1 | 12/2005 | Beaudoin et al. |
| 2006/0021300 A1 | 2/2006 | Tada et al. |
| 2006/0137298 A1 | 6/2006 | Oshita et al. |
| 2006/0224137 A1 | 10/2006 | McCabe et al. |
| 2006/0265867 A1 | 11/2006 | Schaap |
| 2007/0074953 A1 | 4/2007 | McCabe |
| 2008/0077418 A1 | 3/2008 | Coleman |
| 2008/0223537 A1 | 9/2008 | Wiedmann |
| 2009/0020211 A1 | 1/2009 | Andrews et al. |
| 2010/0078119 A1 | 4/2010 | Yamamoto |
| 2010/0078120 A1 | 4/2010 | Otsubo |
| 2010/0078127 A1 | 4/2010 | Yamamoto |
| 2010/0193138 A1 | 8/2010 | Eckstein |
| 2010/0193155 A1 | 8/2010 | Nakatani |

FOREIGN PATENT DOCUMENTS

| | | |
|---|---|---|
| CA | 1153345 | 9/1983 |
| CA | 1190078 | 7/1985 |
| CA | 1210744 | 9/1986 |
| CA | 1212132 | 9/1986 |
| CA | 1236056 | 5/1988 |
| CA | 1249102 | 1/1989 |
| CA | 1292201 | 11/1991 |
| CA | 1307244 | 9/1992 |
| CA | 1308015 | 9/1992 |
| CA | 1310342 | 11/1992 |
| CA | 2023816 | 3/1994 |
| CA | 2404154 | 10/2001 |
| CA | 2541194 | 1/2006 |
| CA | 2559517 | 5/2007 |
| CA | 2337700 | 8/2008 |
| CA | 2407867 | 6/2010 |
| DE | 60123502 | 10/2006 |
| DE | 60216550 | 12/2006 |
| DE | 102005048868 | 4/2007 |
| DE | 102006047280 | 4/2007 |
| EP | 0044206 | 1/1982 |
| EP | 0048011 | 3/1982 |
| EP | 0089106 | 9/1983 |
| EP | 0099732 | 2/1984 |
| EP | 0206208 | 12/1986 |
| EP | 0304140 | 8/1987 |
| EP | 0439897 | 2/1990 |
| EP | 0455231 | 11/1991 |
| EP | 510251 | 10/1992 |
| EP | 0652175 | 5/1995 |
| EP | 0811473 | 12/1997 |
| EP | 0901780 | 3/1999 |
| EP | 1132325 | 9/2001 |
| EP | 1199057 | 4/2002 |
| EP | 1272347 | 1/2003 |
| EP | 1366734 | 12/2003 |
| EP | 0990588 | 5/2004 |
| EP | 1571249 | 9/2005 |
| EP | 1619008 | 1/2006 |
| EP | 1707168 | 4/2006 |
| EP | 1726414 | 11/2006 |
| EP | 1302424 | 12/2006 |
| EP | 1801045 | 6/2007 |
| EP | 1941853 | 9/2008 |
| EP | 2233116 | 9/2010 |
| EP | 2238955 | 10/2010 |
| ES | 509706 | 11/1982 |
| ES | 520559 | 12/1983 |
| ES | 296211 | 12/1987 |
| ES | 200601373 | 7/2009 |
| ES | 2311349 | 9/2009 |
| FR | 2177355 | 11/1973 |
| FR | 2252961 | 7/1975 |
| FR | 1132325 | 10/2006 |
| FR | 2891811 | 4/2007 |
| GB | 191101501 | 0/1912 |
| GB | 439897 | 12/1935 |
| GB | 856389 | 12/1960 |
| GB | 941073 | 11/1963 |
| GB | 1096373 | 12/1967 |
| GB | 1126539 | 9/1968 |
| GB | 1346329 | 2/1974 |
| GB | 1412812 | 11/1975 |
| GB | 2045298 | 10/1980 |
| GB | 2115775 | 9/1983 |
| GB | 2288316 | 10/1995 |
| IT | 1374910 | 5/2010 |
| IT | 1374911 | 5/2010 |
| JP | 428364 | 5/1990 |
| JP | 6197925 | 1/1991 |
| JP | 626161 | 5/1991 |
| JP | 542180 | 8/1991 |
| JP | 576566 | 9/1991 |
| JP | 626160 | 7/1992 |
| JP | 10-277091 | 4/1997 |
| JP | 9299398 | 11/1997 |
| JP | 10035621 | 2/1998 |
| SE | 0602047 | 5/2007 |
| SE | 0601003-7 | 6/2007 |
| SE | 0601145-6 | 10/2009 |
| WO | WO9403301 | 2/1994 |
| WO | WO9732552 | 9/1997 |
| WO | WO9747265 | 12/1997 |
| WO | WO 9747810 | 12/1997 |
| WO | WO9821134 | 5/1998 |
| WO | WO 9907319 | 2/1999 |
| WO | WO 9913813 | 3/1999 |
| WO | WO9932385 | 7/1999 |
| WO | WO 9965437 | 12/1999 |
| WO | WO 0143682 | 6/2001 |
| WO | WO 0172237 | 10/2001 |
| WO | WO0172237 | 10/2001 |
| WO | WO2004007329 | 1/2004 |
| WO | WO 2005075163 | 1/2005 |
| WO | WO2007029115 | 3/2007 |
| WO | WO2007039800 | 4/2007 |
| WO | WO2007126347 | 11/2007 |
| WO | WO2008001209 | 1/2008 |
| WO | WO2008155618 | 12/2008 |

OTHER PUBLICATIONS

USPTO Office Action regarding U.S. Appl. No. 11/083,765, dated Sep. 10, 2007, 7 pages.
USPTO Office Action regarding U.S. Appl. No. 11/083,765, dated Mar. 1, 2007, 6 pages.
USPTO Office Action regarding U.S. Appl. No. 11/083,765, dated Apr. 16, 2008, 14 pages.
USPTO Office Action regarding U.S. Appl. No. 11/083,765, dated Nov. 18, 2008, 16 pages.
USPTO Office Action regarding U.S. Appl. No. 11/083,765, dated Jun. 15, 2009, 12 pages.
USPTO Notice of Allowance regarding U.S. Appl. No. 11/083,765, dated Oct. 13, 2009, 11 pages.
USPTO Office Action regarding U.S. Appl. No. 12/583,042, dated Oct. 21, 2010, 5 pages.
USPTO Notice of Allowance regarding U.S. Appl. No. 12/583,042, dated Jan. 10, 2011, 6 pages.

METHOD OF PRODUCING A PANTS-TYPE DIAPER

RELATED APPLICATION

This is a continuation of U.S. patent application Ser. No. 12/583,042, filed 13 Aug. 2009, now U.S. Pat. No. 7,909,956, which is a continuation application of U.S. patent application Ser. No. 11/083,765, filed 18 Mar. 2005, now U.S. Pat. No. 7,638,014, which claims the benefit of U.S. Provisional Patent Application Ser. No. 60/573,648, filed 21 May 2004, and entitled "Method of Producing a Pants-Type Diaper."

BACKGROUND OF THE INVENTION

The present invention relates to disposable undergarments and, more specifically, to methods and apparatuses for forming disposable undergarments.

Generally, disposable undergarments such as pants-type diapers are made up of two nonwoven layers of material with elastic strands of material placed between the two nonwoven layers of material thus creating an elastic web laminate. The layers of material are continuous sheets of material that are eventually cut into individual undergarment lengths. The elastic strands may be arranged and cut so that specific areas of the undergarment are free of elastic tension or forces. An absorbent pad, often contained within an insert or core is then also placed into the pants-type diaper product.

To insure the pants-type diaper retains a proper shape and to hold all of the added layers of the diaper, reinforcing layers and backing materials are normally added to the continuous sheets of material, with the reinforcing layers corresponding to the cut elastic strands of each individual blank. Each of these layers needs to be adhesively joined at some point in the manufacturing process to the elastic web laminate to form the completed undergarment.

One such method to produce a disposable undergarment is shown in Umebayashi, U.S. Appl. No. 2003/013518. The application discloses a process of producing a disposable undergarment wherein a layer of elastic material is adhered between two nonwoven layers. Further along the assembly process, a reinforcing material is added to the layers, followed by an absorbent pad, and then a backing layer is added to the above combined layers. While this process will produce a disposable undergarment, it has been observed that there may potentially be more efficient ways of producing the disposable undergarments.

SUMMARY OF THE INVENTION

The present invention provides for a method and apparatus for producing disposable undergarments. Compared to previous designs and processes, the present invention results in less material use, less material waste, higher line speeds and higher efficiencies due to an improved overall process.

The process provides a single roll of nonwoven material, which is slit into two equal segments. The segments are then routed and guided so that they overlap one another, with a layer of elastic material also being fed between the two segments. The nonwoven segments and the elastic strands are then pressed together. The resulting web laminate will be slit again, providing two separate elasticized nonwoven laminates that will be combined with an outer nonwoven material to form a complete chassis web assembly.

An outer nonwoven backing material and one or two optional graphic applique panels are combined and pressed together at a separate station along the assembly line. A separate backing/appliqué panel web assembly will be combined with each of the nonwoven/elastic layers. The two separate nonwoven/elastic layers and the backing/appliqué panel layers are then pressed and adhesively joined together to form a chassis web for disposable undergarments. The web may have absorbent pads (typically contained within an insert or core) or other decorative material added along the process. The resulting undergarments are formed from a process that uses less material and is more efficient than previous methods.

DESCRIPTION OF THE PREFERRED EMBODIMENT

Although the disclosure hereof is detailed and exact to enable those skilled in the art to practice the invention, the physical embodiments herein disclosed merely exemplify the invention, which may be embodied in other specific structures. While the preferred embodiment has been described, the details may be changed without departing from the invention.

Figure 1:
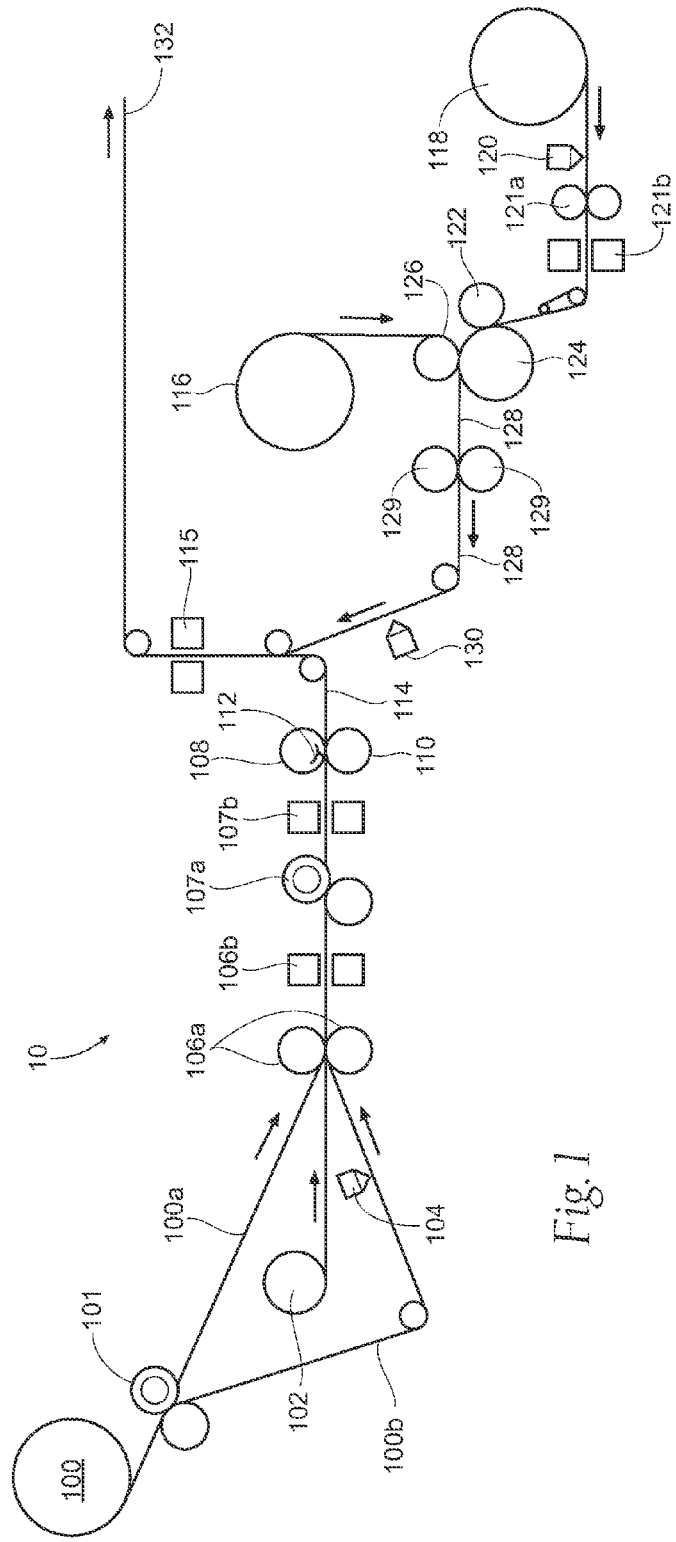
FIG. 1 is a diagrammatic illustration of a method of producing undergarments according to the present invention.

FIG. 1 shows a diagrammatic illustration of an embodiment of the present invention. A system 10 for producing the chassis assembly for disposable undergarments is shown. FIG. 1 shows two segments or layers of nonwoven material 100a and 100b, slit by slitter 101 from a common roll 100, preferably having equal widths, fed into the system 10. A roll or layer or strands of elastic material 102 are also fed into the system 10, with the elastic material 102 being fed intermediate of the two nonwoven layers of material 100a and 100b. An adhesive applicator 104 applies an adhesive coating to one of the layers of nonwoven material 100a or 100b. Alternatively, the adhesive coating may be applied to both nonwoven layers 100a and 100b, or to the elastic material 102. The design of the nonwoven materials 100a and 100b and the elastic material 102 should determine where and how the adhesive applicator applies an adhesive to the system 10, and any arrangement should not be considered a limiting factor. The adhesive applicator 104 may supply a hot melt adhesive or any other suitable adhesive that will sufficiently adhere the elastic material 102 to the layers of nonwoven material 100a and 100b. The nonwoven layers 100a and 100b and the elastic material 102 are then fed through a pair of pressing rollers 106a to securely bind the elastic material 102 to the nonwoven layers 100. The nonwoven layers 100a and 100b and the elastic material 102 are next fed through an edge folder 106b. After being pressed together and having the edges folded, the layers 100a, 100b, and 102 are then fed through a slitting station 107a and a spreader assembly 107b to position these separate elasticized web laminates on new process lines. These newly centered webs are then each fed through a cutting roller 108 and an anvil roller 110. The anvil roller 110 supplies resistance for the cutting roller 108, which has cutting means 112 located on its exterior surface. The cutting means 112 cuts through one layer of the nonwoven layers 100 and severs the elastic material 102 positioned between the nonwoven layers. The cutting means 112 may cut both nonwoven layers 100a and 100b, but it is preferable that only layer 100a is severed. Layer 100a refers only to the layer near the cutting means 112 and should not be limited to any spatial orientation. A resultant web of material 114 is formed having predetermined individual areas with and without elastic material on or elastic forces in the web 114.

Still referring to FIG. 1, a second feed area is located on the right side of the schematic. A web of backing material 116 is fed into the system 10. Also, a web of graphically printed material 118 is fed into the system 10. An adhesive applicator 120, similar to the adhesive applicator 104, will apply an adhesive material to the graphically printed material 118. The graphically printed material 118 will proceed through a slitting station 121a and a web spreader assembly 121b before encountering a cutting roll 122 and a pressing or transfer roll 124. The pressing/transfer roll 124, along with another transferring roll 126, will transfer the graphically printed material 118 onto the backing material 116. Further along the process, a pair of pressing rolls 129 will assist in binding the backing material 116 and the graphically printed material 118 together, resulting in a second web of material 128. Provided the backing material 116 and the graphically printed material 118 are adequately secured to one another after passing the transferring roll 126, the pressing rolls 129 may not be necessary in the system. It should be noted that the graphically printed material 118 can be slit and separated prior to or after the adhesive applicator 120 so that ultimately graphics can appear on both front and back of the finished pants type diaper.

Figure 1B:
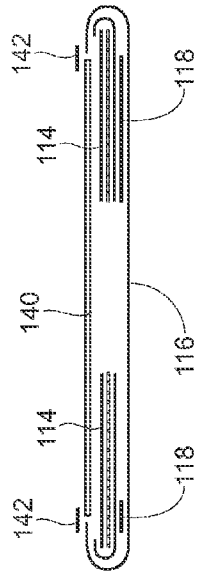
FIG. 1B is a cross-sectional view of the resulting web further including an insert or core and cover strips.
Figure 1A:
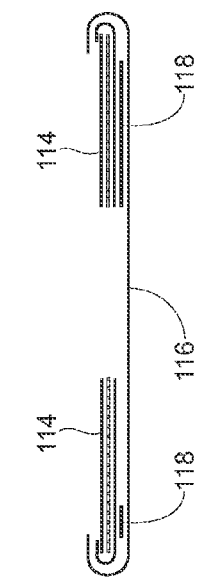
FIG. 1A is a cross-sectional view of the resulting web.

A third adhesive applicator 130, similar to the previously mentioned adhesive applicators 120 and 104, applies an adhesive to the second web of material 128 after the graphically printed material and the backing material have been combined. The second web of material 128 and the resultant webs of material 114 are then pressed together and the edges are folder at second edge folder 115, forming a final web 132 that comprises all of the previous layers. The final web 132 as shown in FIG. 1A will proceed for further modifications, such as adding decorative material, absorbent material, or cutting of leg holes, if not previously added, folding, sealing and severing the web 132 into individual undergarments. As shown in FIG. 1B, the final web may have an insert or core 140 placed between the inwardly folded edges of the nonwoven material 100. In addition, one or more cover strips 142 may be adhered to conceal the junction of the edges and the insert.

Figure 2:
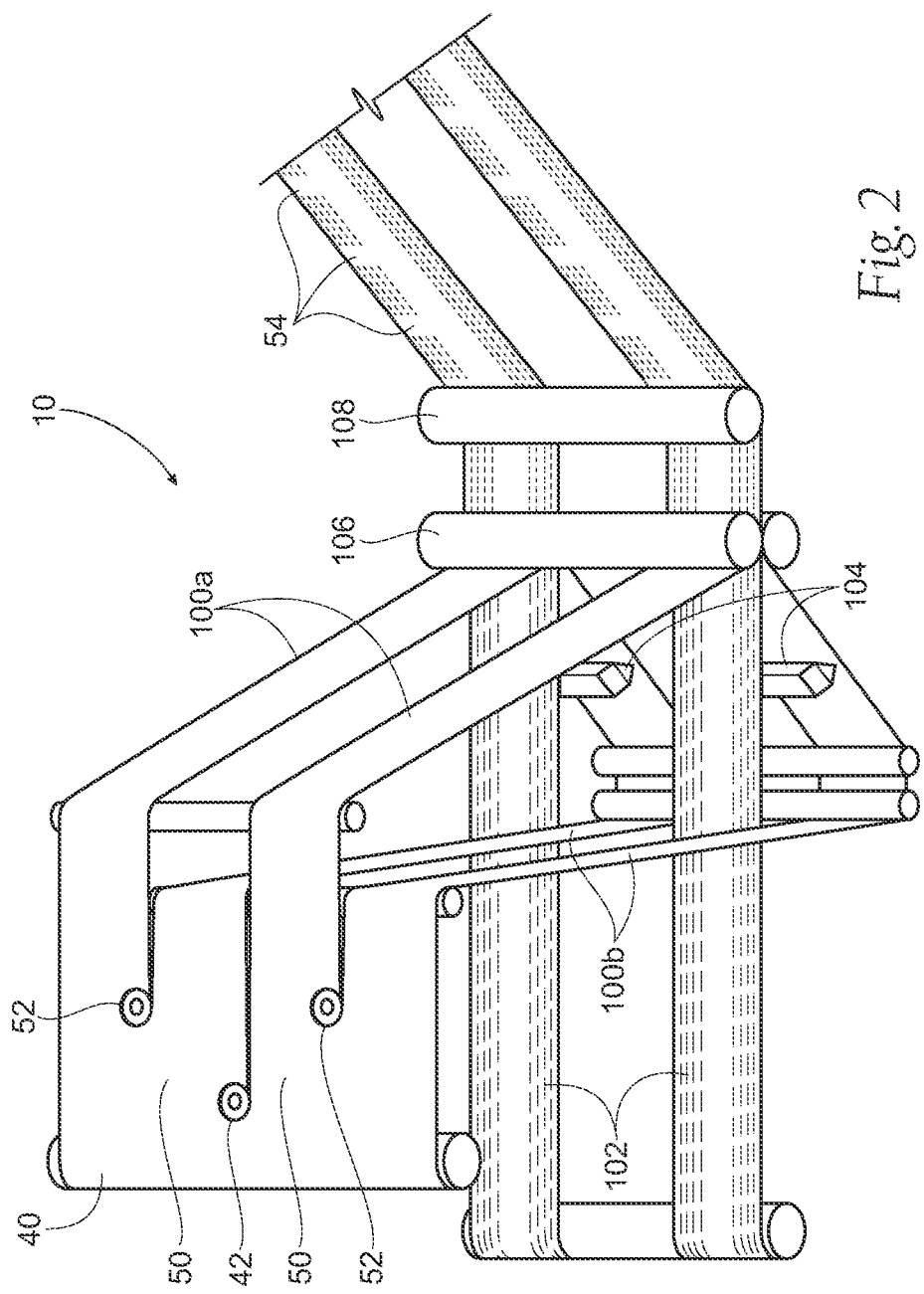
FIG. 2 is a schematic representation of a section of an alternate assembly process according to the present invention.

FIG. 2 is an alternate schematic representation of the introductory feed area of the present system. A single preliminary layer of nonwoven material 40 provides a starting point for the system 10. The preliminary layer 40 proceeds towards a first slitting device 42, which will cut the preliminary layer 40 into a pair of feeder layers 50. The feeder layers 50 each form the basis of an eventual final web 132 (see FIGS. 1A and 4). As previously stated, the preliminary layer 40 provides for two systems 10 shown in FIG. 1, as understood in the present invention to run concurrently. The feeder layer 50 proceeds towards a second slitting device 52, which will cut and slit the feeder layer 50 into the nonwoven layers 100a and 100b, preferably with the nonwoven layers 100a and 100b having equal widths. The four nonwoven layers, two layers 100a and two layers 100b, are separated and fed into the system 10 on opposing sides of the two elastic layers 102, with a nonwoven layer 100a and 100b supplied for each elastic layer 102. As shown the adhesive applicator 104 applies an adhesive to one of the nonwoven layers 100 that results from each of the feeder layers 50 after being slit by the second slitting device 52. However, it is possible the adhesive applicator 104 may provide adhesive prior to the layers proceeding to the pressing roller 106.

Still referring to FIG. 2, the pressing roller 106 and the cutting roller 108 are shown to be sufficiently wide enough so that single rollers may be used to process all of the layers. While this is preferred for efficiency and cost purposes, it is possible to have individual rollers for each set of combined layers and still fall within the scope of the present invention.

Figure 3:
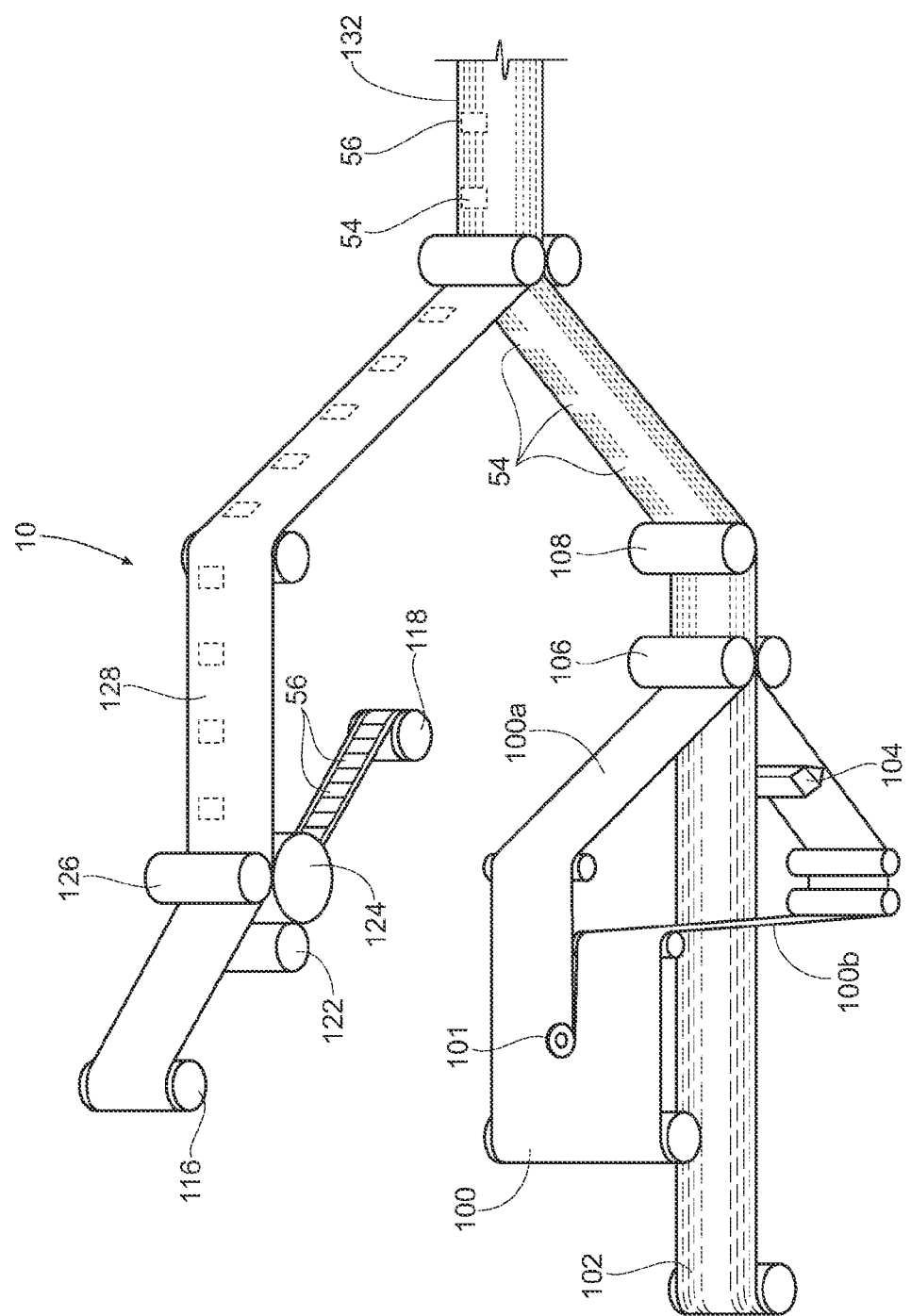
FIG. 3 is a schematic view of a method and apparatus that may be used to produce undergarments in accordance with the present invention.

FIG. 3 provides a further schematic representation of a full width chassis assembly fabrication system 10 similar to that shown in FIG. 1. Like elements are denoted by like reference numerals. The nonwoven layers 100a and 100b originate from the single feeder layer of material 100. The feeder layer 100 proceeds towards the second slitting device 101, which will cut and slit the feeder layer 100 into the nonwoven layers 100a and 100b, preferably with the nonwoven layers 100a and 100b having equal widths, which are then separated and fed into the system 10 on opposing sides of the elastic layer 102. The elastic layer 102 is a stretched sheet, which may be made up of threads, scrims, elastic sheets, or other elastic materials that will provide elastic properties for the undergarments. An adhesive material is applied to the nonwoven layers 100a and 100b and the elastic layer 102, as previously described in FIG. 1. Likewise, as discussed with respect to FIG. 2, adhesive material may be applied to anywhere before the layers 100a, 100b, and 102 encounter the pressing roll 106. The layers 100a, 100b, and 102 are fed through the pressing rolls 106. Each respective web is then fed through each cutting roller 108. The cutting roller 108 is not necessarily limited to devices that cut the elastic material 102, but also may include die presses, ultrasonic methods, or heated presses that will remove the elastic material 102 (or the elastic forces) from a specific predetermined area 54 on the nonwoven layers 100.

Still referring to FIG. 3, the backing material 116 and the graphically printed material 118 are shown being fed together through the transfer roll 124 and the pressing roll 126. As previously noted with respect to FIG. 1, the web of graphically printed material 118 passes the cutting roll 122. The cutting roll 122 will cut the graphically printed material into specific graphically printed sections 56 of predetermined area. The web of graphically printed material 118 is preferably fed into the system at a slower rate than that of the backing material 116, for instance by controlling the speed of the feed roll for material 118. A slower feed rate allows the graphically printed sections 56 to be cut to a shorter length and spaced apart from one another in a distance that will correspond to one graphically printed section per an individual undergarment. Each of the resulting graphically enhanced sections 56 will be approximately the same size as that of the area 54 having the elastic material 102 removed. Preferably, the graphically enhanced sections 56 will be slightly larger than the areas 54, to insure that the graphically enhanced section adequately covers the elastic force free area 54. The second web of material 128 exiting the transfer roll 124 and the press roll 126 displays such an arrangement. The final web of material 132 includes the graphically enhanced sections 56 aligned with the areas where the elastic material 102 was removed. It should again be noted that the graphically printed material 118 can be slit and separated prior to or after hot melt application so that graphics can appear on both front and back of the finished pants-type diaper.

Figure 4:
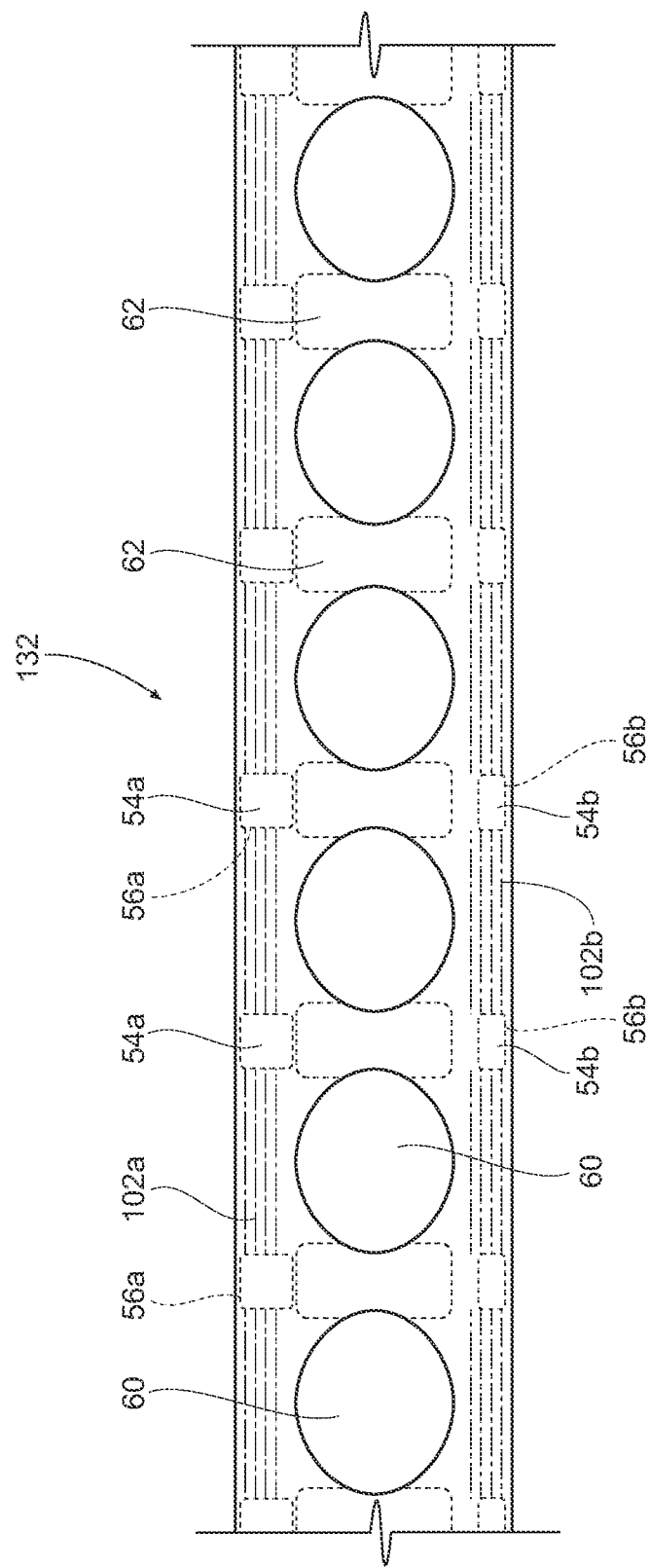
FIG. 4 is a top planar view of a resultant layer formed according to the present invention.

The final web of material 132 can be viewed in FIG. 4. As shown, the final web 132 has leg holes 60 cut from the final web 132 and, also, an absorbent layer of material 62 added to the final web 132. It is understood that the leg holes 60 and the absorbent layer 62 may be added at varying positions during the undergarment formation process. The graphically enhanced sections 56a correspond to the areas 54a, which are located where the elastic layers 102a are positioned on the final web 132. FIG. 4 shows the elastic layers 102b as non-continuous elements that are interrupted by additional non-adhered areas 54b and the graphically enhanced sections 56b. It will be understood that non-adhered sections 54b and graphically enhanced sections 56b could be omitted on the elastic layers 102b and still fall within the scope of the present invention. It will also be understood that the final web 132 may be designed without the elastic layer 102b present.

Figure 5:
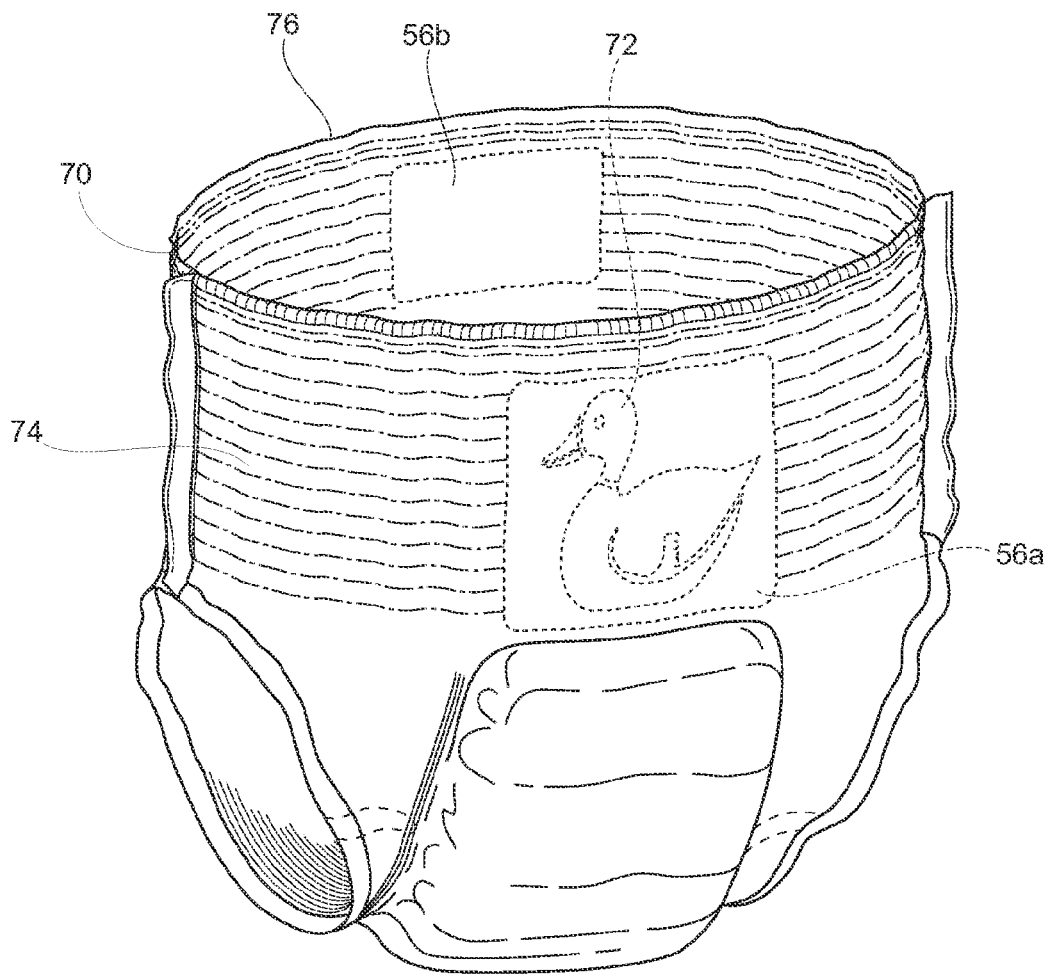
FIG. 5 is a finished disposable undergarment produced according to the present invention.

A single resultant undergarment 70 is shown in FIG. 5. The undergarment 70 has the graphically enhanced sections 56a and 56b displayed. A decorative design 72 may appear on the graphically enhanced section 56a. The undergarment is shown with a graphically enhanced section 56a located on a front side 74 of the undergarment 70 and a second section 56b located on the opposite side 76 of the undergarment 70. If desired, only one graphically enhanced section may be formed in each undergarment 70. In the case of two graphically enhanced sections 56a and 56b, the system would operate as previously shown and described with respect to the previous figures, except that the graphically printed web of material 118 would be divided into separate strips, or possibly two webs of material 118 would be fed into the system. Likewise, when the elastic material 102 passes the cutting roller 108, the cutting roller 108 would remove a second section of elastic material 102 that would correspond to the backside 76 of the undergarment 70.

The method described and shown has advantages over prior art designs. Providing a layer consisting of nonwoven material and elastic material separate from a layer consisting of the backing material and the graphically enhanced material provides for a system that improves overall process control as compared to prior art designs. Generally, the process adheres together two separate layers to form a portion of the final garment web. Prior designs have a first layer, with every subsequent layer of material adhered separately to the first layer. Thus, each time a new layer is added, such as the backing material or the graphically enhanced material, another possible chance for misalignment or nonadherance arises. The present method minimizes the potential for such errors, which also leads to higher line speeds and material savings.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A method of making an undergarment, the method comprising the steps of:
providing at least two elasticized web laminates made from a method comprising the steps of:
providing an elastic sheet material and a first and second oppositely disposed layer of non-woven fabric material;
adhering said elastic material to said facing sides of said first and second layers of nonwoven fabric material, thereby forming an elasticized web laminate;
slitting the elasticized web laminate into the at least two elasticized web laminates;
severing a pre-selected portion of said elastic material in at least one of the at least two elasticized web laminates;
providing a second web of material made from a method occurring substantially simultaneously as the method of making the at least two elasticized web laminates, the method comprising the steps of:
providing a graphically printed material having a predetermined area exceeding the area of said severed portion of said elastic material;
providing a sheet of backing material;
adhering said graphically printed material to one side of said sheet of backing material; and
merging and adhering said at least two elasticized web laminates to said second web of material wherein said graphically printed material is aligned with and extends over said severed portion of said elastic material, thereby forming an assembled chassis web.

2. The method according to claim 1 further including the step of adhering an absorbent pad to said assembled chassis web.

3. The method according to claim 1 further including the steps of:
providing a feeder layer of nonwoven material; and
slitting said feeder layer of nonwoven material to form said first and second layers of nonwoven material.

4. A method of making an undergarment, the method comprising the steps of:
providing at least two elasticized web laminates made from a method comprising the steps of:
providing an elastic sheet material and a first and second oppositely disposed layer of non-woven fabric material;
adhering a first portion of said elastic material to said facing sides of said first and second layers of nonwoven fabric material to define a second non-adhering portion of said elastic sheet material, thereby forming an elasticized web laminate;
slitting the elasticized web laminate into the at least two elasticized web laminates;
severing said second portion of said elastic material from said first portion of said elastic material in at least one of the at least two elasticized web laminates;
providing a second web of material made from a method occurring substantially simultaneously as the method of making the at least two elasticized web laminates, the method comprising the steps of:
providing a graphically printed material having a predetermined area exceeding the area of said second non-adhering portion of said elastic material;
providing a sheet of backing material;
adhering said graphically printed material to one side of said sheet of backing material; and
merging and adhering said at least two elasticized web laminates to said second web of material wherein said graphically printed material is aligned with and extends over said non-adhering portion of said elastic material, thereby forming an assembled chassis web.

5. The method according to claim 4 further including the step of adhering an absorbent pad to said assembled chassis web.

6. The method according to claim 4 further including the steps of:
   providing a feeder layer of nonwoven material; and
   slitting said feeder layer of nonwoven material to form said first and second layers of nonwoven material.

* * * * *